United States Patent [19]

Boehme

[11] 4,397,681

[45] Aug. 9, 1983

[54] FOLIAR ANTITRANSPIRANT

[75] Inventor: Werner R. Boehme, Glen Ellyn, Ill.

[73] Assignee: Fats and Proteins Research Foundation, Inc., Des Plaines, Ill.

[21] Appl. No.: 271,526

[22] Filed: Jun. 8, 1981

[51] Int. Cl.$^3$ ............................................. A01N 25/00
[52] U.S. Cl. ........................................ 71/106; 71/79; 71/DIG. 1
[58] Field of Search ...................... 71/DIG. 1, 106, 79

[56] References Cited

U.S. PATENT DOCUMENTS 3,197,299 7/1965 Stull et al. ................... 71/DIG. 1 X

OTHER PUBLICATIONS

Praendl et al., Chem. Abs., vol. 80, (1974), 13809x.
Delors., Chem. Abst., vol. 80, (1974), 19400d.
Cavoski et al., Chem. Abst., vol. 80, (1974), 69306y.
Lyr et al., Chem. Abst., vol. 88, (1978), 100359j.
Mayr et al., Chem. Abst., vol. 87, (1977), 113000q.

Primary Examiner—Catherine L. Mills

[57] ABSTRACT

A foliar antitranspirant and methods of both reducing moisture loss from green plant tissues and of simultaneously treating leafy plant surfaces with incompatible materials are based on an emulsion of animal fat material and water. A surface active agent is included for emulsifying the animal fat material and the water; and this surfactant possesses an hydrophile-lipophile balance number of from about 3 to about 13. Plant treatment materials may be individually incorporated in the oil phase, the water phase or both prior to spraying of the emulsion on plant surfaces.

11 Claims, No Drawings

4,397,681

FOLIAR ANTITRANSPIRANT

FIELD OF THE INVENTION

This invention relates generally to the science of increasing the utility of agricultural corps and more particularly to compositions which can be spray-applied to agricultural crops for reducing moisture loss.

BACKGROUND OF THE INVENTION

It is known, for example, that the exhalation or emission of water vapor from the surface of green tissues in living plants facilitates the absorption of aqueous nutrients by the roots and additionally promotes necessary gaseous interchange between plant tissues and the external air. However, in semi-arid geographic regions, maximum crop production is limited by a combination of the cost and availability of irrigation water and the water-use efficiency of the particular varieties of agricultural plants being grown. As a consequence, the modern phenomena of diminished water supplies and rising energy costs required to pump irrigation water have lead to the commercial introduction of antitranspirant materials based on emulsified waxes and polyolefins. These compositions have proved capable of decreasing plant transpiration; but care must be exercised in their use both to prevent phytotoxicity, as exhibited for example by leaf burn, and to avoid actual diminution in crop yields.

BRIEF DESCRIPTION OF THE INVENTION

The present invention contemplates a sprayable emulsion of animal tallow and water for application to field crops; and the compositions of the invention have been found to reduce the crop usage of water significantly and to increase the resistance of plant leaf surfaces to the loss of moisture vapor. In addition, the present compositions are non-toxic to growing plants and serve to increase crop yields in semi-arid region agriculture.

Accordingly, a general object of the invention is to provide a new and improved surface-coating composition for use in connection with agricultural field crops.

Another object of the invention is to provide a crop antitranspirant that is based on naturally occurring, instead of petroleum-derived substances.

These and other objects and features of the invention pertain to the particular substances and formulations whereby the foregoing objects are attained.

DETAILED DESCRIPTION OF THE INVENTION

The compositions of the instant invention are desirably prepared as emulsified concentrates to be stored and shipped as such and diluted on-site with water for field application. In formulating the emulsified concentrates of the invention, a surfactant or mixture of surfactants is selected to exhibit the required hydrophile-lipophile balance, and a quantity of an animal fat material, such as beef tallow, is melted and stirred in a jacketed kettle or similar vessel until a completely liquified state is stabilized at an appropriate temperature, for example 45° C.

The surface active ingredient, in its commercially received state, is then added to the molten fat and blended to a uniform mixture. Thereafter, water, suitably softened if necessary and heated to the temperature of the liquified fat, is introduced in continuation of stirring until the mixture thickens forming a water-in-oil emulsion. When approximately three-quarters of the water has been added, the mixture converts to an oil-in-water emulsion as indicated by a decrease in viscosity. Next, the remaining water fraction is rapidly incorporated with agitation; and the resultant composition is quickly cooled to a suitable temperature of about 25° C. At this point, the product is ready for either use or packaging and storage.

The surface active agent or emulsifier ingredient of the invention is selected to exhibit a hydrophile-lipophile balance number of from about 3 to about 13 and preferably between 4 and 8; and the more free fatty acid which is present as a constituent of the selected animal fat ingredient, the lower generally is the required hydrophile-lipophile balance number. The surface active agent for use in the practice of the invention desirably excludes cationics; and the various products commercially available under the trademarks "Span" and "Tween" have proved eminently useful in this regard. Thus, suitable surface active agents include complex esters and esterethers having, as starting points, various hexahydric alcohols, alkylene oxides a fatty acids. As is well known, the "Span" products are partial esters of fatty acids containing from 8 to 18 carbon atoms, commonly from about 12 to 18 carbon atoms, and hexitol anhydrides derived from sorbitol, whereas the "Tween" materials are derived from the "Span" products by adding polyoxyethylene chains to the non-esterified hydroxyls. These products are also commercially advantageous because their basic raw material is of animal, rather than petroleum origin. The surface active agent sold under the trademark "Amway APSA" and surfactant mixtures containing 2-diethylaminoethanol have proved unsuitable for use in the practice of the present invention. Caseinate emulsifiers and soaps made in situ may, however, be employed in the practice of the present invention.

The particular level of surfactant is not critical in the practice of the present invention; and from about 5% to about 15% surfactant in the emulsified concentrate has proved both effective and economical.

In compliance with features of the invention, the selected animal fat material is a mixture of monoglycerides, diglycerides and triglycerides in which mixture there is present a quantity of one or more fatty acids in the free or uncombined state; and specific fatty substances which have proved useful in the practice of the invention include such inedible animal body fats as Choice White Grease, No. 1 Dark Tallow, No. 2 Dark Tallow, Yellow Grease and Bleachable Fancy Tallow. Tallows are preferred in the practice of the invention; and tallow fatty acids may be added under some circumstances in an amount on the order of about 10–20% by weight. Hydrogenated tallow also has utility in formulating the present compositions.

The animal fat material is included in the instant compositions at a level of from about 20% to about 60% by weight of the emulsified concentrate, optimized in a range of from about 25% to about 55% by weight thereof; and for agricultural field application, a rate of 7.5 pounds of tallow per acre, sprayed as an oil-in-water emulsion containing from 1.5 to 12% tallow by weight, has proved effective in reducing green plant transpiration.

Water serves as a convenient vehicle and diluent in the practice of the invention; and a water supply with a low content of dissolved minerals is desired so as to minimize composition with the surfactant as an emulsifier. Because the compositions of the invention comprise both oil and water phases, they constitute highly convenient media for the simultaneous application of either water-miscible or oil-miscible agricultural chemicals, or both; and such products as fungicides, trace mineral nutrients, and insecticides can be readily incorporated with the instant compositions for foliar application. Savings in labor and in both equipment time and fuel may be made in this manner. In particular the fungicide N-(trichloromethylthio)-4-cyclohexene-1,2-dicarboximide ("Captan") can be incorporated in the oil phase of the instant compositions for foliar application.

EXAMPLES 1 AND 2

Antitranspirant compositions in accordance with the invention were prepared as follows:

FORMULA 1

| Ingredient | Parts By Weight |
|---|---|
| tallow | 24 |
| Span 60 (sorbitan monostearate) | 2.7 |
| Tween 20 (polyoxyethylene sorbitan monolaurate) | 0.3 |
| water | 73 |
| | 100.0 |

FORMULA 2

| Ingredient | Parts By Weight |
|---|---|
| tallow | 24 |
| Span 40 (sorbitan monopalmitate) | 2.7 |
| Tween 60 (polyoxyethylene sorbitan monostearate) | 0.3 |
| water | 73 |
| | 100.0 |

These formulated products were evaluated on newly sprouted Russet potato plants greenhouse-grown in mini-lysimeters. Sixty-six plants were selected from a lot of approximately one-hundred plants of like age based on uniformity of appearance, foilage, and previous water use. The experimental design was a randomized complete block with six replications, excepting the control group which has two replications in each randomized block. Blocks were oriented in a north-south direction in the greenhouse to minimize the effects of differential lighting and temperature due to natural shading and proximity of some plants to the walls of the greenhouse. Plant observation such as diffusivity and water potential were selected from treatments in the central four blocks of the experimental design. Plants for the late spraying trials were selected from the forty plants not selected for the first spraying. The experimental design for the late spraying was a completely randomized block with three replications; and blocks were oriented in a north-south direction.

The formulations for the first spraying were applied with a hand-pump sprayer while the second and late spraying were applied using an air-pressurized system. A more uniform application of the formulations was achieved with the pressurized method. No clogging of the pressurized sprayer occurred when this latter method was used, although some clogging of the hand-sprayer had been observed in the previous applications.

The total water-usage data is set forth in Table I. The application rate was 50 ml. of the emulsion per plant.

TABLE I

| Treatment and Dilution (% solids by wht.) | | Total Water-Use (in milliliters) Before 1st Spraying 14-Day Total | After 1st Spraying 3rd Day | 6th Day | 12th Day | After 2nd Spraying 4th Day | 7th Day |
|---|---|---|---|---|---|---|---|
| F1[1] | 2% | 10856 | 908 | 1453 | 6601 | 1307ab[4] | 1063bcd |
| | 4% | 10540 | 964 | 1404 | 6638 | 1270ab | 996abcd |
| | 6% | 10745 | 983 | 1402 | 6655 | 1372bc | 858a |
| | 8% | 10192 | 882 | 1362 | 6447 | 1067a | 912abc |
| F2[2] | 2% | 9986 | 857 | 1343 | 6085 | 1312ab | 900ab |
| | 4% | 10936 | 1152 | 1573 | 6854 | 1307ab | 1073bcd |
| | 6% | 11239 | 1030 | 1502 | 6917 | 1333bc | 1103cd |
| | 8% | 10916 | 858 | 1623 | 6628 | 1557c | 922abcd |
| commercial product 2%[3] | | 11269 | 962 | 1512 | 6941 | 1300ab | 1030abcd |
| Control | | 10540 | 1038 | 1411 | 6586 | 1329bc | 1179d |

[1]Formula 1 product.
[2]Formula 2 product.
[3]"Folicote".
[4]Numbers with different lower case letters are significantly different at .95 Duncan's Multiple Range Test.

Comparison of the foregoing data indicates that the beneficial effects of the first spraying were temporary but that the water-use, after the second spraying, was significantly reduced by Formula 1 at the 8% level as soon as four days after the second treatment. In addition, Formula 1 at the 6% level and Formula 2 at both the 2% and the 8% levels resulted in significantly lower water take-up rates seven days after the second treatment.

The total water-usage data which were collected in the late spraying studies are set forth in Table II:

TABLE II

| Treatment and Dilution (% solids by wht.) | Total Water-Use (in milliliters) Before Spraying 3-day total | After Spraying 4-day total |
|---|---|---|
| F1 8% | 2760 | 2550 |
| F1 12% | 2608 | 2294 |
| F2 8% | 2764 | 2294 |
| F2 12% | 2530 | 2114 |
| commercial antitranspirant 3% | 3044 | 2488 |
| control | 3060 | 2780 |

The data collected after spraying demonstrates that water-usage was decreased significantly by Formula 1 at the 12% level and that, on the basis of a percentage of the control value, all treatments showed a decrease in water-usage.

Leaf diffusive resistance studies showed that the Formula 2 treatment at the 6% level significantly increased the upper leaf surface resistance whereas the Formula 2 product at the 6% level significantly increased lower leaf surface resistance upon re-treatment of the plants.

EXAMPLES 3, 4, 5 AND 6

Dilute antitranspirant compositions were formulated and sprayed on field-grown Russet potato plants at two locations in the Texas High Plains, a region typical of semi-arid agricultural, potatoes being exemplary of plants having restricted root systems not noted for aggressive foraging ability. The specific formulations are set forth hereinbelow. Two essentially similar foliar applications were made on June 26, 27 and July 10, 11 respectively; and total gallonage of the water was 100 gallons per application at the Lubbock Site and 85 gallons per application at the Olton Site.

Tensiometer measurements were employed to schedule irrigation at the Lubbock Site, and the two moisture levels were 0–60 cb. (dry) and 0–30 cb. (wet). The dry and wet levels received 24.8 and 39.7 inches of irrigation water respectively; and a total of 6.26 inches of rain fell. The cumulative water at the Lubbock Site ranged from 20.1 to 20.4 inches in the dry level and from 33.1 to 33.6 inches in the wet level.

At the Olten Site, irrigation water was scheduled by the producer and applied with a pivot sprinkler system.

| Example No. | Active Ingredient | Antitranspirant Application Rate (lbs./A.) | |
|---|---|---|---|
| | | Active | Emulsifier* |
| LUBBOCK SITE | | | |
| 3 | tallow | 12.3 | 1.5 |
| 4 | tallow | 24.6 | 3.1 |
| 5 | tallow | 49.2 | 6.2 |
| — | commercial product** | (24.6 combined) | |
| OLTON SITE | | | |
| 6 | tallow | 13.9 | 1.7 |
| — | commercial product** | (13.9 combined) | |

*90% Span 60 and 10% Tween 20.
**"Folicote".

The potato crops were harvested from the several test plots and yield data were collected and are set forth in Table III below:

TABLE III

Average Yield (in cwt./A.) and Estimated Crop Value of Potatoes By Grade

| Treatment | Grade | | | Value($/A.*) |
|---|---|---|---|---|
| | <4 oz. | 4–8 oz. | >8 oz. | |
| LUBBOCK SITE | | | | |
| Wet moisture level: | | | | |
| Example 3 | 134 | 140 | 44 | 2684 |
| Example 4 | 134 | 151 | 83 | 3542 |
| Example 5 | 154 | 176 | 62 | 3430 |
| commercial product | 162 | 165 | 63 | 3369 |
| control | 172 | 153 | 64 | 3306 |
| Dry moisture level: | | | | |
| Example 3 | 148 | 95 | 32 | 2086 |
| Example 4 | 139 | 102 | 25 | 2001 |
| Example 5 | 144 | 101 | 16 | 1858 |
| commercial product | 136 | 83 | 26 | 1816 |
| control | 141 | 90 | 24 | 1872 |
| OLTON SITE | | | | |
| Example 6 | 89 | 101 | 38 | 2012 |
| commercial product | 82 | 97 | 41 | 1995 |
| control | 79 | 75 | 24 | 1474 |

*Crop values are estimated from the base price of $4, $10, and $17 per cwt. for <4 oz., 4–8 oz., and >8 oz. grades respectively and disregarded tuber defects and marketability.

Examination of the foregoing data shows that treatment with the antitranspirant compositions of the invention was generally as effective as treatment with the commercial product and, in the case of the formulas of Example 3 and Example 4 at the low moisture level at the Lubbock Site, as well as the formula of Example 6 at the Olten Site, were notably more effective. It was observed that marketability of all yields was adversely affected by severe regrowth caused by irrigation subsequent to moisture stress.

EXAMPLES 7 THROUGH 12

Additional compositions were formulated as follows:

FORMULA 3

| Ingredient | Parts By Weight |
|---|---|
| bleachable fancy tallow | 200 |
| Tween Mos 100K Special | 14.4 |
| Tween 60 | 1.6 |
| Span 60 | 4.0 |
| | 220.0 parts |

The foregoing ingredients were melted together at 60° C. A solution of 45 parts denatured alcohol (SD-40), 135 parts deionized water and 0.4 g of 50% dispersible, commercial "Captan" powder was added slowly with vigorous agitation and the dispersion was circulated through a Logeman homogenizer until the temperature of the emulsion fell to 33° C. The resulting product was a white, easily pourable emulsion.

When diluted to 1% solids with water, the composition of Formula 3 gave a milky dispersion that exhibited only slight creaming after standing for several days at room temperature, indicating that a product sufficiently stable for field-spraying had been produced.

FORMULAS 4, 5, 6 and 7

| Ingredient | Parts By Weight |
|---|---|
| yellow grease | 70 |
| undistilled tallow fatty acids | 7 |
| butylated hydroxyanisole (BHA) | 0.008 |
| 1:1 mixture of methyl and propyl p-hydroxybenzoates | 0.008 |
| citric acid | 0.008 |
| total | 77.024 parts |

The listed materials were melted together at 55° C. With stirring, 2.9 parts of ammonium hydroxide (28–30% ammonia) was added slowly below the surface of the melt and followed by 112.5 parts of deionized water at 55° C. The mixture was circulated through an orifice homogenizer until the temperature had fallen to 30° C. The product was a heavy, pourable cream which was easily diluted further with water to give a homogenous dispersion.

Sprayable emulsions were likewise obtained when the ammonium hydroxide was replaced by 2.5 parts of potassium hydroxide, 7 parts of triethanolamine, and 4 parts of morpholine.

FORMULA 8

| Ingredient | Parts By Weight |
|---|---|
| sodium caseinate | 87 |
| sodium benzoate | 0.5 |
| total | 87.5 parts |

These two ingredients were dispersed in 460 parts of water with gentle warming. Bleachable fancy tallow (400 parts) was melted at 50° C. and slowly blended into the caseinate dispersion with good agitation and recirculated through a colloid mill until the temperature fell to 33° C.

The resultant product was a viscous, pourable white emulsion which dispersed readily upon further dilution with water.

The specific examples herein described are to be considered as being primarily illustrative. Various changes will, no doubt, occur to those skilled in the art;

and such changes are to be understood as forming a part of this invention insofar as they fall within the spirit and scope of the appended claims.

The invention is claimed as follows:

1. The method of reducing moisture loss from green plant tissues of agricultural field crops which comprises the step of coating plant leaf surfaces with an emulsion of animal fat material.

2. The method of reducing moisture loss from green plant tissues according to claim 1 wherein said animal fat material is tallow.

3. The method of reducing moisture loss from green plant tissues according to claim 1 wherein said animal fat material is hydrogenated tallow.

4. The method of reducing moisture loss from green plant tissues of agricultural field crops according to claim 1 wherein said animal fat material defines an oil phase and wherein said emulsion further includes water defining an aqueous phase in cooperation with said oil phase, and a surface active agent for emulsifying said animal fat material and said water and having a hydrophile-lipophile balance number of from about 3 to about 10, said surface active agent including a fatty acid ester in which the fatty acid radicals contain from 8 to 18 carbon atoms.

5. The method according to claim 4 wherein said hydrophile-lipophile balance number is from about 4 to about 8.

6. The method according to claim 4 wherein said surface active agent is non-ionic.

7. The method according to claim 4 wherein said surface active agent comprises a fatty acid partial ester of hexitol anhydride in which the fatty acid alkyl radicals contain from 12 to 18 carbon atoms.

8. The method according to claim 7 wherein said surface active agent further comprises a polyoxyethylene condensation product of said partial ester.

9. The method according to claim 4 wherein said surface active agent is soap.

10. The method according to claim 4 wherein said oil phase is the discontinuous phase.

11. The method according to claim 4 wherein said aqueous phase is the discontinuous phase.

* * * * *